United States Patent [19]

Higashi et al.

[11] Patent Number: 4,955,900

[45] Date of Patent: Sep. 11, 1990

[54] INTRA-OCULAR LENS

[75] Inventors: Kazumi Higashi; Toshio Nakajima; Atsushi Hino; Sunao Inoue, all of Osaka, Japan

[73] Assignees: Nitto Denko Corporation, Osaka; Menicon Co., Ltd., Aichi, both of Japan

[21] Appl. No.: 363,694

[22] Filed: Jun. 9, 1989

[30] Foreign Application Priority Data

Jun. 10, 1988 [JP] Japan .................. 63-144470

[51] Int. Cl.$^5$ ........................... A61F 2/16
[52] U.S. Cl. ........................... 623/6; 528/185
[58] Field of Search .............. 623/6, 5; 528/185

[56] References Cited

U.S. PATENT DOCUMENTS

| | | | |
|---|---|---|---|
| 3,959,350 | 5/1976 | Rogers | 528/185 |
| 4,198,714 | 4/1980 | Jensen | 623/6 |
| 4,450,593 | 5/1984 | Poler | 623/6 |
| 4,601,720 | 2/1986 | Sinskey | 623/6 |
| 4,612,361 | 9/1986 | Peters | 528/185 |
| 4,737,322 | 4/1988 | Bruns et al. | 723/6 X |

Primary Examiner—Ronald Frinks
Attorney, Agent, or Firm—Sughrue, Mion, Zinn, Macpeak & Seas

[57] ABSTRACT

An intra-ocular lens comprising a lens part and a fixing part is disclosed, said lens part comprising a colorless transparent polyimide consisting mainly of a repeating unit represented by formula (I):

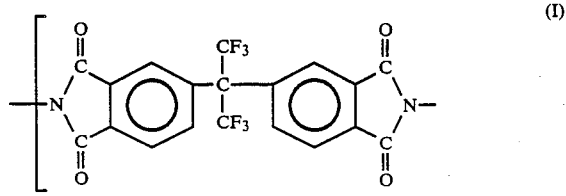

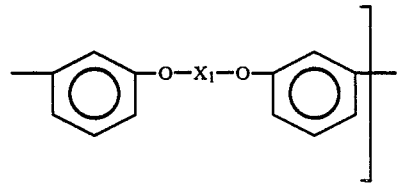

wherein $X_1$ represents

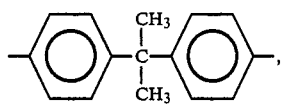

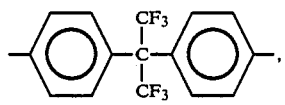

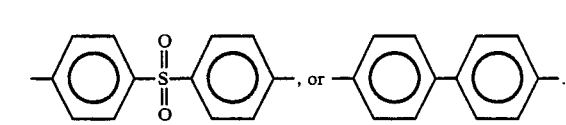

The intra-ocular lens exhibits compatibility with the organism, chemical inactivity, and insusceptibility to modification or deterioration by the organism, has a refractive index of 1.6 or higher, completely absorbs ultraviolet rays while exhibiting substantial transparency to visible rays, and possesses heat resistance enough to withstand autoclaving.

4 Claims, 1 Drawing Sheet

FIG. 1
FIG. 2
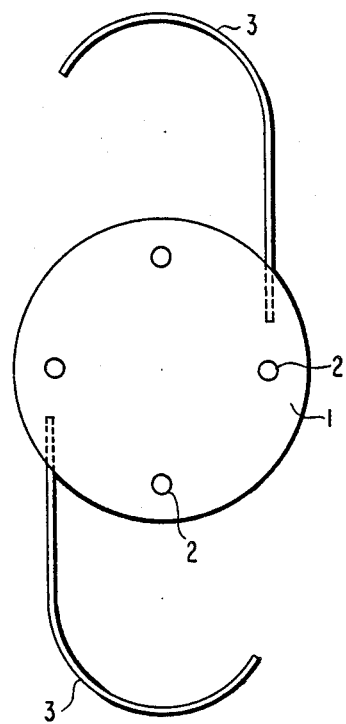

INTRA-OCULAR LENS

FIELD OF THE INVENTION

This invention relates to an intra-ocular lens (artificial crystalline lens) which can be implanted in the anterior or posterior chamber of an aphakic eye after extraction of the crystalline lens, for example, extraction of cataract, to recover vision.

BACKGRROUND OF THE INVENTION

Methods of recovery of vision (correction of refraction) of a patient with aphakia due to extraction of the crystalline lens, such as cataractoperation include use of glasses, application of a contact lens, and implantation of an intra-ocular lens.

Correction of vision by glasses endows an aphakic eye with visual power, but the patient suffers from defects of a visual field (enlargement of a retinal image), the so-called Jack-in-the-box phenomenon, and the like and must endure these diadvantages for a certain term before he can make good use of them. In case of hemiaphakia, binocular visual functions cannot be obtained due to anisoiconia.

Application of a contact lens is effective to anisoiconia. Contact lenses have ever found difficulty in continuous use in an eye, but this problem has been nearing a solution owing to the recent developments of soft contact lenses of high water conent which permit of continuous use. Under the present situration, however, partly because most of patients with cataract are older persons and partly because handling of contact lenses is troublesome, only few of them make actual use of the contact lens as prescribed after the operation.

Hence, use of glasses or a contact lens is not accepted as a favorable method of correction of vision.

Implantation of an artificial crystalline lens is a technique that has been performed since 30 years ago. An artificial, crystalline lens, i.e., an intra-ocular lens, is advantageous in many aspects such that it is less causative of enlargement of a retinal image, causes no defect of a visual field or ring scotoma, provides binocular vision functions (particularly advantageous for hemiaphakia), requires no time for a patient to get accustomed to, and involves no handling once implanted. With the recent developments of microscopes and ultrasonic knives, the implantation technique has been improved, and the shape and materials of the intra-ocular lens have also been improved. The intra-ocular lens will thus be increasing its importance as a means for correction of vision of aphakic eyes.

Although an intra-ocular lens is very excellent in vision correction, because it is a foreign matter to the eye, it is occasionally complicated by a disturbance of the endothelium of the anterior chamber, which results in incompensation, sometimes leading to blindness. Materials of intra-ocular lenses are therefore required to have no toxicity to eyes, excellent compatibility to organism, and insusceptibility to modification or deterioration by the organism.

Natural light have wavelenghts in the ultraviolet, visible through infrared regions. Transmission of a large quantity of ultraviolet rays into the eyes has a danger of inducing retinopathy, and the crystlalline lens preferentially absorbs ultraviolet rays, serving to protect the retina. In this connection, transmission of ultraviolet rays in the aphakia gives rise to a serious problem. Therefore, the material of intra-ocular lenses should absorb ultraviolet rays in the range of from 200 to 380 nm while transmitting visible rays of from 380 to 780 nm. In addition, since a heavy intra-ocular lens would be a burden to the eye, the material is demanded to have an essentially small specific gravity and, for making the lens thinner, a high refractive index.

The most widely current material of intra-ocular lenses is polymethyl methacrylate (hereinafter abbreviated as PMMA). PMMA possesses excellent optical characterisitcs, resistance to acids, alkalis and organic solvents, and aging resistance.

However, since PMMA lacks heat stability as having a glass transition temperature (Tg) of 100° C. or less, it cannot be subjected to autoclaving for sterilization which is usually conducted at 121° C. and 1.2 atms. for about 1 hour. Under such autoclaving conditions, PMMA is softened and deformed, becoming useless. Accordingly, intra-ocular lenses comprising PMMA are subjected to gas sterilization using ethylene oxide gas, etc. Since gas sterilization causes the gas to remain in the lens, and the lens containing the gas is liable to cause mucosal inflammation when implanted in the eye as it is. Therefore, the gas sterilization of the lens should be inevitably followed by degassing taking about 2 weeks, which increases the cost over the autoclaving. Further, PMMA transmits a considerable quantity of ultraviolet rays and thereby probably induces damages of the retina as stated above. It has been proposed to solve this problem by addition of a ultraviolet absorbent as disclosed in JP-A-60-233149 (the term "JP-A" as used herein means an "unexamined published Japanese patent applicaton"). However, use of a ultraviolet absorbent is not recognized as a favorable method because there is a fear that the ultraviolet absorbent added to PMMA may reduce transmission of visible rays, too, and also it gradually oozes out from the lens to adversely affect the surrounding tissues. Furthrmore, PMMA has a relatively low refractive index (about 1.49) as compared with glass so that the PMMA lens should have a large thickness and possibly adheres to the iris to cause complications.

Considering the above-described various demerits of PMMA inspite of their many merits, studies have been directed to other materials capable of being subjected to autoclaving, exhibiting ultraviolet asorptivity, and having a high refractive index. For example, glass has a high refractive index and absorbs ultraviolet rays. Nevertheless, it is not suitable for use as an intra-ocular lens because of its difficulty in processing and its high specific gravity (2.5), giving a burden to the eye. Natural crystalline or synthetic materials such as sapphire, ruby, corundum, silicone, and diamond also exhibit a ultraviolet absorbing power but are unsuitable due to difficulty of processing and high specific gravities similarly to glass. Hence, an interest in synthetic resins as a substitution for PMMA has increased in recent years, and polysulfone, polyarylate, polyether-imide, etc. have been studies. Polysulfone and polyarylate both have a high refractive index, absorb ultraviolet rays, and can be sterilized by autoclaving (softening point of polysulfone: 175° C.) but have not been put into practical use due to difficulty of processing. Although polyether-imide exhibits satisfactory processability as well as high refractive index, ultraviolet absorptivity, and capability of autoclaving, it is yellow- to yellowish brown-colored, resulting in too a low transmittance to visible light and, therefore, subserves no practical use as an intra-ocular lens.

Under these circumstances, despite the above-mentioned disadvantages, PMMA has been made use of as a material of intra-ocular lenses by applying expensive gas sterilization and adding a ultraviolet absorbent that has a possibility of giving adverse influences optically and biologically, merely because no satisfactory substitution therefor has not been found.

Therefore, it has been keenly demanded to develop a material for intra-ocular lenses which can easily be processed into a thin lens by machining or molding, has a specific gravity of not more than 1.7, preferably not more than 1.5, and a refractive index of not less than 1.5, preferably not less than 1.6, exhibits chemical stability and compatibility with the organism, absorbs ultraviolet rays dangerous to the retina, and possesses heat resistance enough to withstand autoclaving.

SUMMARY OF THE INVENTION

One object of this invention is to provide an intra-ocular lens exhibiting excellent compatibility with the organism and ultraviolet absorbing properties, having a small specific gravity and a high refractive index as recited above, having chemical stability, and possessing heat resistance enough to withstand autoclaving.

As a result of extensive investigations of a series of synthetic resins, the inventors have reached a finding that an aromatic polyimide is superior to PMMA in perfect ultravioelt absorptivity, high refractive index (1.6 or higher), and sufficient heat resistance for autoclaving. The aromatic polyimide is nevertheless colored in yellow to brown so that it absorbs not only ultraviolet rays but most of visible rays. The inventors have hence continued their study on an aromatic polyimide resin having no visible light absorptivity. As a result, it has now been found that an aromatic polyimide consisting mainly of a repeating unit represented by formula (I) shown below provides an intra-ocular lens which perfectly absorbs ultraviolet rays while transmitting most of visible rays, having substantial transparency. It was confirmed that the lens made of this particular aromatic polyimide possesses various characteristics required for intra-ocular lenses similarly to the conventional aromatic polyimides. The present invention has been completed based on these findings.

The present invention relates to an intra-ocular lens comprising a lens part and a fixing part, said lens part comprising a colorless transparent polyimide consisting mainly of a repeating unit represented by formula (I):

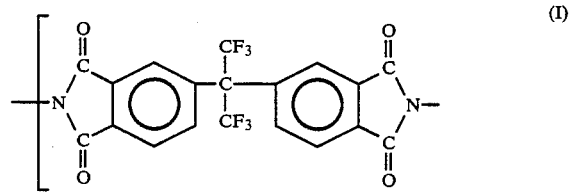

(I)

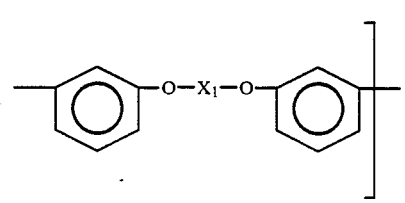

wherein $X_1$ represents 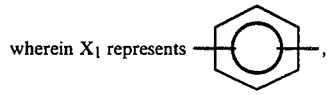,

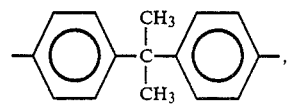

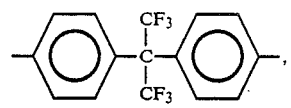

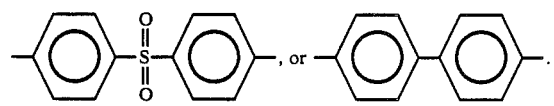, or

The lens part of the intra-ocular lens according to the present invention exhibits compatibility with the organism, chemical inactivity, and insusceptibility to modification or deterioration by the organism, has a refractive index of 1.6 or higher, completely absorbs ultraviolet rays in the region of from 200 to 380 nm while exhibiting substantial transparency to visible rays in the region of from 380 to 780 nm, and possesses heat resistance enough to withstand autoclaving.

BRIEF DESCRIPTION OF THE DRAWINGS

FIG. 1 is a plane view of the intra-ocular lens according to the present invention which is to be buried in the posterior chamber of a human eye.

FIG. 2 is a side view of the intra-ocular lens of FIG. 1.

DETAILED DESCRIPTION OF THE INVENTION

The intra-ocular lens according to the present invention comprises a lens part and a fixing part for fixing the lens part in a human eye. The lens part comprises a colorless transparent polyimide consisting mainly of a repeating unit represented by formula (I) shown above.

The colorless transparent polyimide according to the present invention can be obtained by, for example, reacting 2,2-bis(3,4-dicarboxyphenyl)hexafluoropropane dianhydride represented by formula (II):

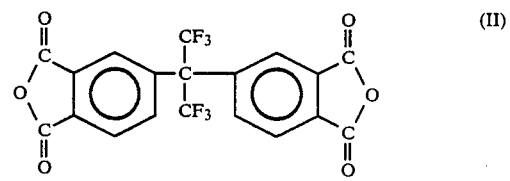

(II)

and an aromatic diamino compound having an amino group at the m-position thereof as represented by formula (III):

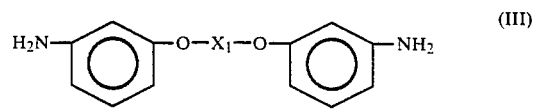

(III)

wherein $X_1$ is as defined above.

Specific examples of the aromatic diamine of formula (III) include:

1,4-bis(3-aminophenoxy)benzene of formula:

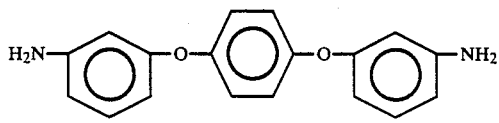

1,3-bis(3-aminophenoxy)benzene of formula:

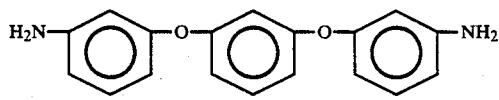

2,2-bis[4-(3-aminophenoxy)phenyl]propane of formula:

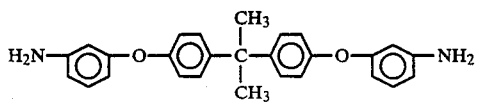

2,2-bis[4-(3-aminophenoxy)phenyl]hexafluoropropane of formula:

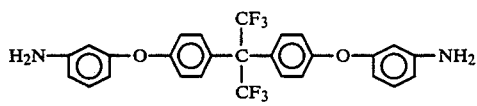

bis[4-(3-aminophenoxy)phenyl]sulfone of formula:

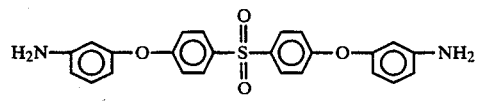

and 4,4'-bis(3-aminophenoxy)biphenyl of formula:

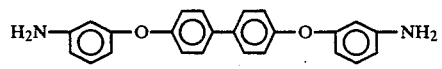

These aromatic diamines may be used either individually or in appropriate combinations of two or more thereof.

A combination of the above-described 2,2-bis(3,4-dicarboxyphenyl)hexafluoropropane dianhydride of formula (II) and the aromatic diamine of formula (III) can provide a colorless transparent polyimide consisting mainly of the repeating unit represented by formula (I). The term "mainly consisting of" as used herein includes a polymer consisting solely of the repeating unit of formula (I). The higher the content of the repeating unit of formula (I), the higher the colorless transparency of the polyimide. The least ultraviolet absorption properties and visible light transmission properties as demanded in the present invention can be assured as long as the polyimide contains at least 80 mol% of the repeating unit of formula (I). That is, with this condition being met, aromatic tetracarboxylic acid dianhydrides other than the 2,2- bis(3,4-dicarboxyphenyl)hexafluoropropane dianhydride and diamino compounds other than the aromatic diamino compounds having an amino group at the m-position thereof may also be used in combination. A preferred content of the repeating unit of formula (I) is more than 80 mol%, and more preferably 95 mol% or more.

The other aromatic tetracarboxylic acid dianhydrides which can be used in combination include pyromellitic acid dianhydride, 3,3',4,4'-biphenyltetracarboxylic acid dianhydride, 3,3',4,4'-benzophenonetetracarboxylic acid dianhydride, 4,4'-oxydiphthalic acid dianhydride, 4,4'-bis(3,4-dicarboxyphenoxy)diphenylsulfone dianhydride, 2,2-bis(3,4-dicarboxyphenyl)hexafluoropropane dianhydride, 2,3,6,7-naphthalenetetracarboxylic acid dianhydride, 1,2,5,6-naphthalenetetracarboxylic acid dianhydride, and 1,4,5,8-naphthalenetetracarboxylic acid dianhydride. These aromatic tetracarboxylic acid dianhydrides may be used either individually or in combinations thereof.

The other diamino compounds which can be used in combination include 4,4'-diaminodiphenyl ether, 3,4'-diaminodiphenyl ether, 4,4'-diaminodiphenylsulfone, 4,4'-diaminodiphenylmethane, 4,4'-diaminobenzophenone, 4,4'-diaminodiphenylpropane, p-phenylenediamine, benzidine, 3,3'-dimethylbenzidine, 4,4'-diaminodiphenyl thioether, 3,3'-dimethoxy-4,4'-diaminodiphenylmethane, 3,3'-dimethyl-4,4'-diaminodiphenylmethane, 2,2-bis(4-aminophenyl)propane, and 2,2-bis[4-(4-aminophenoxy)phenyl]hexafluoropropane. These compounds may be used either individually or in combinations thereof.

The colorless transparent polyimide of the present invention can be synthesized by copolymerizing the above-described aromatic tetracarboxylic acid dianhydride(s) and aromatic diamino compound(s) in an organic polar solvent at a temperature not higher than 80° C. to synthesize a polyamido acid, shaping the resulting polyamido acid solution to a desired shape, and treating the resulting shape in air or an inert gas at a temperature of from 50 to 350° C. under atmospheric pressure or reduced pressure to thereby remove the organic polar solvent from the shape by evaporation and, at the same time, convert the polyamido acid to a polyimide (imidation) by dehydration cyclization. Imidation of the polyamido acid and solvent removal may be effected chemically by using a benzene solution of pyridine and acetic anhydride, for example.

It is also possible to convert the polyamido acid to a polyimide by once isolating the polyamido acid by reprecipitation and then causing dehydration cyclization by heating or using a chemical imidating reagent. Further, the polyamido acid solution as synthesized above may be heated as it is to 100° C. or higher for imidation, and a polyamide thus produced can be recovered from the solution as a precipitate. In this case, the formed polyimide precipitated requires filtration and washing but is substantially equal to that obtained above in colorless transparency.

The organic polar solvent to be used for polymerization preferably includes amide type polar solvents, e.g., N,N-dimethylformamide (DMF) and N,N-dimethylacetamide (DMA). Those having a boiling point of 170° C. or less, e.g., DMA, are particularly preferred. The organic solvents may be used either individually or in combinations of two or more thereof. It is not recommended to use N-methyl-2-pyrrolidone as the organic polar solvent because it partially decomposes on heating of the shape of the polyamido acid solution for imidation, and the decomposition product assuming blacky brown tends to remain in the polyimide produced to add a yellowish brown color. Unlike N-methyl-2-pyrrolidone, each of the above-recited organic solvents, e.g., DMA, has a low boiling point so that it vaporizes on heating before it decomposes, causing no coloring of polyimide.

However, the above-described problem associated with N-methyl-2-pyrrolidone used as a polymerization solvent may be eliminated by pouring the resulting polyamido acid solution in a poor solvent for the polyamido acid, e.g., water, to re-precipitate the polyamido acid, which is then converted to a polyimide either as it is in the absence of the polymerization solvent or as re-dissolved in a preferred solvent.

The above-recited preferred organic polar solvent may be appropriately combined with one or more of poor solvents or good solvents which do not impair transparency, such as ethanol, toluene, benzene, xylene, dioxane, tetrahydrofuran, and nitrobenzene, in such a proportion that does not impair solubility. However, too a large proportion of these solvents adversely affects solubility of the polyamido acid produced. It is therefore recommended to limit its proportion in the total solvent to less than 50% by weight, particularly up to 30% by weight.

In the synthesis of the colorless transparent polyimide, it is preferable to control the intrinsic viscosity (logarithmic viscosity number) of the polyamido acid solution between 0.3 and 5.0, more preferably between 0.4 and 2.0, as measured in DMA at a concentration of 0.5 g/100 ml. Too a low intrinsic viscosity results in low mechanical strength of the resulting intra-ocular lens. If it is too high, shaping of the polyamido acid solution to an appropriate shape or isolation of the polyamido acid becomes difficult. From the standpoint of workability, it is preferable to set the polyamido acid solution concentration between 5 and 30%, more preferably between 15 and 25%, by weight.

The intrinsic viscosity as above referred to can be calculated from the following equation, in which the viscosity can be measured by means of a capillary viscometer.

$$\text{Intrinsic Viscosity} = \frac{\text{Natural Logarithm}\left(\frac{\text{Viscosity of Solution}}{\text{Viscosity of Solvent}}\right)}{\text{Polymer Concentration in Solution}}$$

The intra-ocular lens according to the present invention can be produced from the thus prepared colorless transparent polyimide by the following three methods.

A first method comprises casting the polyamido acid solution on a mirror-finished carrier, e.g., a glass plate and a stainless steel plate, to a given thickness and gradually heating it at a temperature of from 100 to 350° C. to cause dehydration cyclization to obtain a polyimide film. The heating for solvent removal and imidation may be carried out continuously. These steps may be performed under reduced pressure or in an inert gas atmosphere. As a modification, the polyamide acid solution cast on the carrier may be dried by heating at 100 to 150° C. for 30 to 120 minutes to form a film, which is then soaked in a benzene solution of pyridine and acetic anhydride to thereby remove the solvent and convert the polyamido acid to polyimide. A plurality of the thus obtained polyimide films are laid up to a prescribed thickness and hot-pressed at 200° to 400° C. under a pressure of from 0.5 to 10 t/cm$^2$ for 0.1 to 10 hours to obtain a transparent polyimide molding, which is then ground to a lens shape by means of a grinding machine.

A second method comprises pouring the polyamido acid solution in a poor solvent, such as water and methanol, to cause re-precipitation, heating the recovered polyamido acid at a temperature of 100 to 350° C. to convert the polyamido acid to a polyimide by dehydration and cyclization, pulverizing the polyimide to obtain a colorless transparent polyimide powder, and molding the powderous polyimide in the same manner as in the first method, i.e., at a temperature of from 200° to 400° C. under a pressure of from 0.5 to 10 t/cm$^2$ for 0.1 to 10 hours. The resulting polyimide molding can be ground to a lens shape in the same manner as in the first method. As a modification, the colorless transparent polyimide powder may be obtained by heating the polyamido acid solution at 100° to 200° C. while stirring to convert it to a polyimide and to precipitate the polyimide. The thus produced polyimide powder can be subjected to hot-pressing only after washing and drying.

In carrying out hot-pressing of the colorless transparent polyimide film or powder as obtained in the first or second method to obtain an intra-ocular lens, the intrinsic viscosity of the resulting intra-ocular lens is preferably set between 0.3 and 4.0, more preferably between 0.4 and 2.0, as measured in 97% sulfuric acid at a concentration of 0.5 g/dl at 30° C., from the standpoint of mechanical strength.

A third method is characterized in that a polyimide molding is obtained directly from the polyamido acid without involving hot-pressing as in the first and second methods. Conventional drying methods have been accompanied by bubbling and have found difficulty in obtaining a homogeneous polyimide molding having a thickness of 150 μm or more. However, when the polyamido acid solution is allowed to stand under reduced pressure for a long period of time and then heated from the inside by the use of far infrared rays or microwaves, there can be obtained a void-free polyimide molding having a thickness of 500 μm or more. That is, utilization of infrared heating or microwave heating enables the polyamido acid to be directly converted to a homogeneous polyimide molding.

The polyimide molding obtained by any of the above-described three methods can be shaped in an intra-ocular lens by, for example, machining. More specifically, the molding is ground to a lens having a curved surface in conformity with a prescribed degree. Holes in which a fixing part is fitted in are made in the lens under numerical control, and a fixing part is fused in the holes by spot welding. One example of the thus produced intra-ocular lens which is to be buried in the posterior chamber of a human eye is shown in FIGS. 1 and 2. The numericals 1, 2, and 3 indicate a lens part, holes for positioning provided in the peripheral portion of the lens part, and a fixing part for fixing the lens part in the eye, respectively.

The shape of the fixing part 3 is subject to wide variation according to necessity. Generally employed materials for the fixing part 3 include polypropylene and polyvinylidene fluoride. In the present invention, the fixing part 3 may be prepared from these and other materials or from the same material as for the lens part.

The intra-ocular lens of the present invention may also be produced by integral molding of a lens part and a fixing part. In this case, the intra-ocular lens has no joint so that there is no possibility of release of the fixing part from the lens part.

The thus produced intra-ocular lens of the present invention exhibits extremely high transparency, entirely differing from those produced from the conventional aromatic polyimide.

The colorless transparent polyimide to be used in this invention, when molded into, for example, a 50 μm-thick film, has a visible light transmittance (at 500 nm) of 80% or more and a yellowness index of 30 or less. The lens part of the intra-ocular lens of the invention, the thickness being, for example, 1 mm, has a total visible light transmittance (total light transmittance) of 60% or more.

Measurement of the ultraviolet-visible spectrum of the lens part of the intra-ocular lens according to the present invention reveals that the point where the transmittance becomes zero (so-called cut-off point) is just at the boundary point between the ultraviolet region and the visible region (i.e., 380 nm) and that the cut-off takes place almost vertically. It seems ascribable to this fact that the lens part perfectly absorbs ultraviolet rays while transmitting the most part of visible rays, i.e., being substantially transparent. Some of the conventional aromatic polyimides other than the colorless transparent polyimide of the present invention have the cut-off point in the vicinity of 380 nm. However, in these polyimides, reduction of transmittance takes place from the much longer wavelength side making a mild slope toward the cupt-off point so that the total light transmittance is markedly reduced, thus making these polyimides useless as an intra-ocular lens material.

As stated above, since the lens part of the intra-ocular lens according to the present invention is produced from a colorless transparent polyimide synthesized from the specific combination of 2,2-bis(3,4-dicarboxyphenyl)hexafluoropropane dianhydride and the aromatic diamine having an amino group at the meta-position thereof, it perfectly absorbs ultraviolet rays in the region of from 200 to 380 nm while exhibing substantial transparency which permits of transmission of the visible light in the region of from 380 to 780 nm. Accordingly, when buried in the eye, it cuts harmful ultraviolet rays to protect the retina while endowing the eye with a sufficient vision. Moreover, the colorless transparent polyimide of the present invention generally has a low specific gravity ranging from 1.3 to 1.4 and a refractive index ranging from 1.6 to 1.7 that is larger than that of the conventional PMMA. Thus, with the degree being equal, the lens part of the invention can be made thinner than that made of PMMA by 30 to 50%, which results in a so much decreased weight. Reduction in thickness and weight of the intra-ocular lens lessens the burden to the eye and diminishes the possiblity of contact with the cornea which may cause complications, thus providing marked safety. In addition, since the colorless transparent polyimide constituting the lens part exhibits the same heat resistance as the conventional aromatic polyimides, the lens part can easily be sterilized by autoclaving to thereby achieving cost reduction.

The intra-ocular lens according to the present invention includes all the applications to the anterior chamber, the posterior chamber, as well as the iris.

The present invention is now illustrated in greater detail by way of the following Examples in view of Comparative Examples, but it should be understood that the present invention is not deemed to be limited thereto.

EXAMPLE 1

1,4'-Bis(3-aminophenoxy)benzene and 2,2-bis(3,4-dicarboxyphenyl)hexafluoropropane dianhydride were reacted at a molar ratio of 1:1 in DMA as a polymerization solvent to prepare a polyamido acid solution having a polyamido acid concentration of 20% by weight.

The polyamido acid solution was cast on a glass plate and heated in a hot air drier at 120° C. for 60 minutes, 180° C. for 60 minutes, 250° C. for 3 hours, and then at 300° C. for 30 minutes for imidation to prepare a polyimide film having a thickness of 50 μm. The infrared absorption analysis of the resulting polyimide film showed an absorption characteristic of an imido group at 1780 cm$^{-1}$ but no absorption of amido acid.

Circular films of 38 mm in diameter were punched out of the polyimide film with a punch cutter, and 20 cut films were piled up and hot-pressed at 300° C. at 1 t/cm$^2$ for 30 minutes to obtain a 1 mm-thick polyimide disc. The disc was found to be a homogeneous structure in which the plurality of films were completely fused together.

The ultraviolet-visible spectrum of the resulting polyimide disc was determined to obtain a wavelength at the cut-off point. Further, the total light transmittance, specific gravity, and refractive index of the disc were determined. The results obtained are shown in Table 1 below. Furthermore, the disc was subjected to pressure cooker test at 121° C. and 1.2 atms. for 24 hours, and the change of appearance was observed. The results of this test are also shown in Table 1.

EXAMPLE 2

A polyimide film was prepared in the same manner as in Example 1, except for replacing 1,4-bis(3-aminophenoxy)benzene with 1,3-bis(3-aminophenoxy)benzene. The infrared absorption spectrum of the polyimide film showed an absorption of imido acid at 1780 cm$^{-1}$ but no absorption of an amido acid.

A 1 mm-thick polyimide disc was produced from the polyimide film in the same manner as in Example 1. The disc was found to be a homogeneous sturcture in which the plurality of films were completely fused together. The resulting polyimide disc was evaluated in the same manner as in Example 1, and the results obtained are shown in Table 1.

EXAMPLE 3

A polyimide film was prepared in the same manner as in Example 1, except for replacing 1,4-bis(3-aminophenoxy)benzene with 2,2-bis[4-(3-aminophenoxy)phenyl]propane. The infrared absorption spectrum of the film showed an absorption of imido group at 1780 cm$^{-1}$ but no absorption of amido acid.

A 1 mm-thick polyimide disc was produced from the polyimide film in the same manner as in Example 1. The disc was found to be a homogeneous structure in which the plurality of films were completely fused together. The disc was evaluated in the same manner as in Example 1, and the results obtained are shown in Table 1.

EXAMPLE 4

A polyimide film was prepared in the same manner as in Example 1, except for replacing 1,4-bis(3-aminophenoxy)benzene with 2,2-bis[4-(3-aminophenoxy)phenyl]hexafluoropropane. The infrared absorption spectrum of the film showed an absorption of an imido group at 1780 cm$^{-1}$ but no absorption of amido acid.

A 1 mm-thick polyimide disc was produced from the resulting polyimide film in the same manner as in Example 1. The disc was found to be a homogeneous structure in which the plurality of films were completely fused together. The disc was evaluated in the same manner as in Example 1, and the results obtained are shown in Table 1.

EXAMPLE 5

A polyimide film was prepared in the same manner as in Example 1, except for replacing 1,4-bis(3-aminophenoxy)benzene with bis[4-(3-aminophenoxy)phenyl]sulfone. The infrared absorption spectrum of the film showed an absorption of imido group at 1780 cm$^{-1}$ but no absorption of amido acid.

A 1 mm-thick polyimide disc was produced from the polyimide film in the same manner as in Example 1. The disc was found to be a homogeneous structure in which the plurality of films were completely fused together. The disc was evaluated in the same manner as in Example 1, and the results obtained are shown in Table 1.

EXAMPLE 6

A polyimide film was prepared in the same manner as in Example 1, except for replacing 1,4-bis(3-aminophenoxy)benzene with 4,4'-bis(3-aminophenoxy)biphenyl. The infrared absorption spectrum of the film showed an absorption of imido group at 1780 cm$^{-1}$ but no absorption of amido acid.

A 1 mm-thick polyimide disc was produced from the polyimide film in the same manner as in Example 1. The disc was found to be a homogeneous structure, in which the plurality of films were completely fused together. The disc was evaluated in the same manner as in Example 1, and the results obtained are shown in Table 1.

COMPARATIVE EXAMPLE 1

A polyimide film was prepared in the same manner as in Example 1, except for replacing 1,4-bis(3-aminophenoxy)benzene with 4,4'-diaminodiphenyl ether and replacing DMA with N-methyl-2-pyrrolidone. The infrared absorption spectrum of the film showed an absorption of imido group at 1780 cm$^{-1}$ but no absorption of amido acid.

A 1 mm-thick polyimide disc was produced from the polyimide film in the same manner as in Example 1. The disc was so much colored that it was impossible to judge whether the plurality of films were completely fused together or not. The disc was evaluated in the same manner as in Example 1 except for the pressure cooker test, and the results obtained are shown in Table 1.

EXAMPLE 7

The polyamido acid solution as obtained in Example 1 was poured into water to re-precipitate the polyamido acid, followed by thoroughly stirring to remove the solvent. The precipitated polyamido acid was collected, washed with methanol, and dried under reduced pressure. The resulting polyamide acid powder was heated in a hot air drier at a temperature up to 250° C. for imidation, followed by pulverization.

The resulting polyimide powder was hot-pressed at 300° C. and 1 t/cm$^2$ for 30 minutes to obtain a 1 mm-thick polyimide molding. The molding was a homogeneous and transparent molding in which the powders were completely fused together. The polyimide molding was evaluated in the same manner as in Example 1, and the results obtained are shown in Table 1.

COMPARATIVE EXAMPLE 2

A polyimide powder was prepared in the same manner as in Example 7, except for using the polyamido acid solution as obtained in Comparative Example 1.

A 1 mm-thick polyimide molding was produced from the resulting polyimide powder in the same manner as in Example 7. This molding was greatly colored, and the powders were not completely fused together into an integral structure.

The resulting polyimide molding was evaluated in the same manner as in Example 1 except for the pressure cooker test. The results obtained are shown in Table 1.

EXAMPLE 8

The polyamido acid solution as obtained in Example 5 was put in a dish and dried at 25° C. under reduced pressure for 24 hours in a vacuum drier. While maintaining the reduced pressure, the polyamido acid was heated with infrared rays at 100° C. for 48 hours, 150° C. for 48 hours, and finally at 250° C. for 24 hours to obtain a polyimide molding having a thickness of 0.8 mm. This molding was found to be transparent and homogeneous.

The resulting polyimide molding was evaluated in the same manner as in Example 1, and the results obtained are shown in Table 1.

COMPARATIVE EXAMPLE 3

A 0.8 mm-thick polyimide molding was prepared in the same manner as in Example 7, except for using the polyamido acid solution as obtained in Comparative Example 1. The resulting molding was found to be homogeneous but was greatly colored.

The polyimide molding was evaluated in the same manner as in Example 1 except for the pressure cooker test, and the results obtained are shown in Table 1.

TABLE 1

| Example No. | Wavelength at Cut-off Point (nm) | Total Light Transmittance (%) | Specific Gravity | Refractive Index | Change of Appearance After Pressure Cooker Test |
| --- | --- | --- | --- | --- | --- |
| Example 1 | 379 | 76 | 1.39 | 1.621 | no change observed |
| Example 2 | 374 | 78 | 1.39 | 1.610 | no change observed |
| Example 3 | 378 | 74 | 1.37 | 1.630 | no change observed |
| Example 4 | 369 | 81 | 1.38 | 1.605 | no change observed |
| Example 5 | 373 | 78 | 1.35 | 1.620 | no change observed |
| Example 6 | 380 | 70 | 1.33 | 1.642 | no change observed |
| Comparative Example 1 | 448 | 0.5 | 1.43 | 1.716 | — |
| Example 7 | 376 | 77 | 1.35 | 1.622 | no change observed |
| Comparative | 447 | 0.5 | 1.37 | 1.698 | — |

TABLE 1-continued

| Example No. | Wavelength at Cut-off Point (nm) | Total Light Transmittance (%) | Specific Gravity | Refractive Index | Change of Appearance After Pressure Cooker Test |
| --- | --- | --- | --- | --- | --- |
| Example 2 | | | | | |
| Example 8 | 372 | 79 | 1.35 | 1.630 | no change observed |
| Comparative Example 3 | 440 | 1.2 | 1.44 | 1.718 | — |

It can be seen from the Table that the polyimide moldings according to the present invention had higher total light transmittances and smaller specific gravities as compared with the comparative polyimide moldings. Further, the comparative moldings had higher refractive indices.

EXAMPLE 9

An intra-ocular lens for a rabbit eye was made from the polyimide molding obtained in Example 8. The fixing part was made separately from a polyvinylidene fluoride resin. Another intra-ocular lens for a rabbit eye was produced in that the fixing part was formed simultaneously with the lens part in one piece from the polyimide molding obtained in Example 8.

The lenses each was buried in the anterior chamber of a rabbit eye, and influences of the lenses on the organism and influences of the organism on the lenses were examined for a period of 6 months. As a result, no toxicity or any harmful influences on the organism was observed for both the lenses. Measurement of optical characteristics of the lenses taken out from the eyes revealed that the characteristics were entirely the same as those before the implantation for both the lenses.

While the invention has been described in detail and with reference to specific embodiments thereof, it will be apparent to one skilled in the art that various changes and modifications can be made therein without deprating from the spirit and scope thereof.

What is claimed is:

1. An intra-ocular lens comprising a lens part and a fixing part, said lens part comprising a colorless transparent polyimide consisting mainly of a repeating unit represented by formula (I):

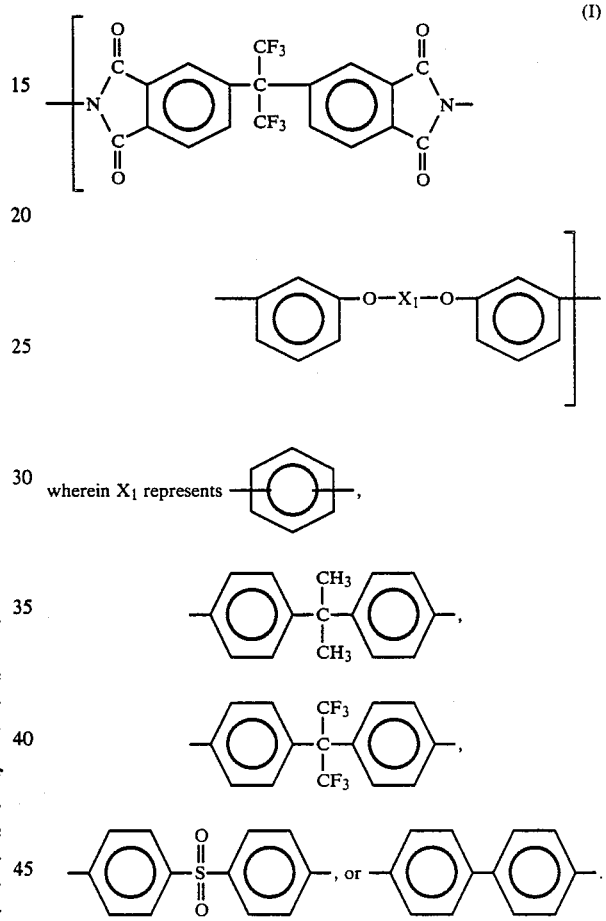

2. An intra-ocular lens as claimed in claim 1, wherein said polyimide contains at least 80 mol% of the repeating unit represented by formula (I).

3. An intra-ocular lens as claimed in claim 1, wherein said polyimide contains at least 95 mol% of the repeating unit represented by formula (I).

4. An intra-ocular lens as claimed in claim 1, wherein said fixing part comprises a colorless transparent polyimide consisting mainly of the repeating unit represented by formula (I), said fixing part and lens part being integrally molded.

* * * * *